(12) United States Patent
Strehlke et al.

(10) Patent No.: US 7,378,522 B2
(45) Date of Patent: May 27, 2008

(54) QUINOLINE, ISOQUINOLINE AND PHTHALAZINE DERIVATIVES AS ANTAGONISTS OF THE GONADOTROPIN-RELEASING HORMONE

(75) Inventors: Peter Strehlke, Berlin (DE); Peter Droescher, Weimar (DE); Ulrich Buehmann, Berlin (DE); Norbert Schmees, Berlin (DE); Peter Muhn, Berlin (DE); Holger Hess-Stumpp, Berlin (DE); Roland Kühne, Berlin (DE); Eckhard Guenther, Maintal (DE); Emmanuel Polymeropoulos, Frankfurt (DE); Antonius M. Ter Laak, Harlem (NL)

(73) Assignee: Zentaris AG, Frankfurt am Main (DE)

( * ) Notice: Subject to any disclaimer, the term of this patent is extended or adjusted under 35 U.S.C. 154(b) by 266 days.

(21) Appl. No.: 10/896,961

(22) Filed: Jul. 23, 2004

(65) Prior Publication Data
US 2005/0004127 A1 Jan. 6, 2005

Related U.S. Application Data

(62) Division of application No. 10/078,530, filed on Feb. 21, 2002, now Pat. No. 6,790,858.

(60) Provisional application No. 60/274,914, filed on Mar. 12, 2001.

(30) Foreign Application Priority Data
Feb. 21, 2001 (DE) ................ 101 08 271

(51) Int. Cl.
*C07D 239/72* (2006.01)
(52) U.S. Cl. ..................... 544/283; 544/284
(58) Field of Classification Search ............... 544/283, 544/284
See application file for complete search history.

(56) References Cited

U.S. PATENT DOCUMENTS

| 5,807,869 A | 9/1998 | Furuya |
| 6,087,503 A | 7/2000 | Furuya et al. |
| 6,150,522 A | 11/2000 | Goulet et al. |

FOREIGN PATENT DOCUMENTS

| HU | 195954 | 5/1987 |
| WO | WO 97 14682 | 4/1997 |
| WO | WO 97 44041 | 11/1997 |

OTHER PUBLICATIONS

International Search Report for International Application No. PCT/EP02/01882 mailed Aug. 14, 2002.

*Primary Examiner*—D. Margaret Seaman
(74) *Attorney, Agent, or Firm*—Millen, White, Zelano & Branigan, P.C.

(57) ABSTRACT

The invention relates to new quinoline, isoquinoline and phthalazine derivatives as antagonists of the gonadotropin-releasing hormone.

13 Claims, No Drawings

QUINOLINE, ISOQUINOLINE AND PHTHALAZINE DERIVATIVES AS ANTAGONISTS OF THE GONADOTROPIN-RELEASING HORMONE

This application is a divisional of U.S. patent application Ser. No. 10/078,530 filed Feb. 21, 2002 now U.S. Pat. No. 6,790,858, which claims the benefit of the filing date of U.S. Provisional Application Ser. No. 60/274,914 filed Mar. 12, 2001, incorporated in their entirety herein.

DESCRIPTION

The gonadotropin-releasing hormone (GnRH) is a hormone that is synthesized predominantly but not exclusively in mammals by nerve cells of the hypothalamus, is transported via the portal vein to the hypophysis and is released in a regulated manner to the gonadotropic cells. By interaction with its receptor that has seven transmembrane domains, GnRH stimulates the production and the release of gonadotropic hormones by means of the second messenger inositol-1,4,5-triphosphate and $Ca^{2+}$ ions. The gonadotropin-luteinizing hormone (LH) that is released by GnRH and the follicle-stimulating hormone (FSH) stimulate the production of sex steroids and the gamete maturation in both sexes. In addition to GnRH (also referred to as GNRH1), there are two other forms of GnRH, namely GnRH2 and 3.

The GnRH receptor is used as a pharmacological target in a number of diseases that are dependent on a functioning sex hormone production, for example prostate cancer, premenopausal breast cancer, endometriosis and uterine fibroids. In the case of these diseases, GnRH superagonists or GnRH antagonists can be used successfully. In particular, the male birth control in combination with a substitution dose of androgens forms a possible further indication.

An advantage of GnRH antagonists in comparison to superagonists is their immediate effectiveness in the blocking of the gonadotropin secretion. Superagonists initially produce an overstimulation of the hypophysis, which results in increased gonadotropin and sex steroid releases.

This hormonal reaction is only completed after a certain delay based on the desensitization and downward-adjustment of the GnRH receptor concentrations. Therefore, GnRH superagonists, both alone and in combination with testosterone, may not be able to suppress effectively sperm production in males and thus are not suitable for male birth control. In contrast to this, peptide GnRH antagonists, especially in combination with a substitution dose of androgen, are able to bring about a significant oligozoospermia in humans.

Peptide GnRH antagonists, however, have a number of drawbacks. They have a considerably lower effectiveness as superagonists and consequently have to be administered at considerably higher dosages. Their oral bio-availability is also low, so that they have to be administered by injection. Repeated injections lead in turn to a reduction in compliance. Moreover, the synthesis of peptide GnRH antagonists in comparison to non-peptide compounds is costly and labor-intensive.

Quinoline derivatives as non-peptide GnRH antagonists are disclosed in, for example, WO97/14682. To date, however, it was not possible to market any non-peptide GnRH antagonists.

The object on which this invention is based consisted in providing new GnRH antagonists that are superior to the known peptide compounds and represent an effective alternative to known non-peptide compounds. The new GnRH antagonists are to have both high effectiveness and high oral bio-availability. In addition, they should be able to be synthesized simply and with as low costs as possible.

This object is achieved by compounds of general formula (1):

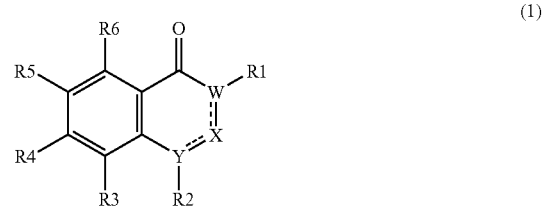

in which

R¹ (a) is an acyl group —CO—R11 or CN, whereby R11 is a saturated, unsaturated, cyclic and/or (hetero)aromatic organic radical, especially a straight or branched alkyl chain with 1-10 C atoms or a phenyl, furan or thiophene group that is optionally substituted by alkyl groups or halogen atoms, (b) is a carboxylic acid ester group —CO—OR12 or a carboxylic acid amide group —CO—NR12R13 or a group —$SO_x$—R12 with X=0, 1 or 2 or —$SO_2$—NR12R13, whereby R12 is a saturated, unsaturated, cyclic and/or (hetero)aromatic organic radical, especially a straight or branched alkyl chain with 1-10 C atoms, an aralkyl group with 7-20 C atoms, whereby the aryl radical optionally can be substituted by alkyl groups or halogen atoms or is a phenyl radical that is optionally substituted by alkyl groups or halogen atoms, and R13 can be a hydrogen atom or a straight or branched alkyl chain with 1-10 C atoms, or (c) is the group -A-NR14-CO—NR15R16, in which A is an alkylene group with 1-4 C atoms, especially with 1 C atom, that is optionally substituted by a $C_1$-$C_6$ alkyl group, a carbonyl group, an oxygen atom or the group —$SO_x$— with X=0, 1 or 2; R14 and R15, in each case independently are a hydrogen atom or a straight or branched alkyl chain with 1-10 C atoms, and R16 is a straight or branched alkyl chain with 1-10 C atoms, a cycloalkyl group with 3-10 C atoms, a cycloalkylalkyl group with 7-20 C atoms, an aralkyl group with 7-20 C atoms, whereby the aryl radical optionally can be substituted by alkyl groups or halogen atoms, a phenyl group that is optionally substituted by alkyl groups or halogen atoms or a heterocyclic ring that is optionally substituted by alkyl groups or halogen atoms, R2 is a group —CH(R21)R22, whereby R21 is a hydrogen atom, a $C_1$-$C_{10}$-alkyl group or an optionally substituted phenyl ring and R22 is an optionally substituted phenyl ring or naphthyl ring, or a group —$CH_2$CH(R23)R24, with R23 and R24 in the meaning of an optionally substituted phenyl ring, R3 and R4 in each case independently are a hydrogen atom or an alkyl group with 1-10 C atoms, and R3 also can be a halogen atom, R5 is a group that is linked via radical Z,

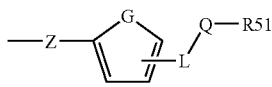

in which G is —C=C—, —C=N—, —N=C—, an oxygen or sulfur atom; Z is a direct bond, an oxygen atom or a sulfur atom, the group CH—R52 or —CHR52—CH—R53—, whereby R52 and R53, independently of one another, have the meaning of a hydrogen atom or an alkyl group and n means numbers 1 and 2, a —C≡C-triple bond or an E- or Z-configured group —CR52=CR53- or C=CR52R53, whereby R52 and R53, independently of one another, have the meaning of a hydrogen atom or an alkyl group, L is a $CH_2$ group or an NH group, Q is a carbonyl or —$SO_x$ group, with X=0, 1 or 2, and R51 is an amino group that is optionally substituted by an alkyl group or a straight or branched alkyl group that is optionally substituted by halogen atoms, hydroxyl or alkoxy groups, or a cycloalkyl group with 3-7 ring members that is optionally substituted by halogen atoms, hydroxyl or alkoxy groups, R6 is the group $CH_2$—N(R61)R62, whereby R61, in each case independently, is a hydrogen atom or an alkyl group, and R62 is an alkyl group or an optionally substituted aralkyl group or a heteroarylalkyl group with 7-20 C atoms, and can mean —W=X=Y— the groups

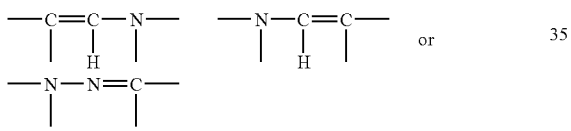

in any orientation; also all stereoisomers of the above-mentioned structures and salts thereof with physiologically compatible acids or bases.

In the compounds of formula (1), by way of example R1 means:

A straight or branched alkyl chain: A methyl, ethyl, n-propyl, iso-propyl, n-, iso-, tert-butyl, n-pentyl, 2,2-dimethylpropyl or 3-methylbutyl group; an n-hexyl, n-heptyl, n-octyl, n-nonyl, n-decyl group. The methyl or ethyl group is preferred.

A phenyl group that is optionally substituted by alkyl groups or halogen atoms: A phenyl group; an o-, m-, p-methyl, ethyl, propyl, or isopropylphenyl group; a 2,3-, 2,4-, 2,5-, 2,6-, 3,4-, 3,5-dimethyl or diethylphenyl group; an o-, m-, p-fluoro-, chloro-, bromo- or iodophenyl group; a 2,3-, 2,4-, 2,5-, 2,6-, 3,4-, 3,5-, difluoro-, dichloro-, dibromo- or diodophenyl group or a naphthyl group. A phenyl group is preferred.

An optionally substituted furan or thiophene group: An unsubstituted 2- or 3-thienyl group; or a 2- or 3-furyl group; or a 3-methyl-, 3-ethyl-, 3-fluoro-, 3-chloro-, 3-bromo-, 3-iodo-2-furyl- or -2-thienyl group; a 4-methyl-, 4-ethyl-, 4-fluoro-, 4-chloro-, 4-bromo-, 4-iodo-2-furyl- or -2-thienyl group; a 5-methyl-, 5-ethyl-, 5-fluoro-, 5-chloro-, 5-bromo-, 5-iodo-2-furyl or -2-thienyl group; a 2-methyl-, 2-ethyl-, 2-fluoro-, 2-chloro-, 2-bromo-, 2-iodo-3-furyl or -3-thienyl group; a 4-methyl-, 4-ethyl-, 4-fluoro-, 4-chloro-, 4-bromo-, 4-iodo-3-furyl- or -3-thienyl group; a 5-methyl-, 5-ethyl-, 5-fluoro-, 5-chloro-, 5-bromo-, 5-iodo-3-furyl- or -3-thienyl group. Preferred is a 2-thienyl or 2-furyl group.

An aralkyl group with 7-20 C atoms: A benzyl group; a 1-phenyl-ethyl-, -propyl-, -butyl-, -hexyl-, -2-methylethyl-, -2-ethylethyl-, -2,2-dimethylethyl group; an o-, m-, p-methyl, ethyl, propyl, isopropylbenzyl group; a 2',3'-, 2',4'-, 2',5'-, 2',6'-, 3',4'-, 3',5'-dimethyl- or -diethylbenzyl group; a 2'-, 3'-, 4'-fluoro-, chloro-, bromo-, iodobenzyl group; a 2',3'-, 2',4'-, 2',5'-, 2',6'-, 3',4'-, 3',5'-, difluoro, dichloro-, dibromo- or diiodobenzyl group or a 2- or 3-naphthylmethyl group; a 2-phenylethyl-, 3-phenyl-propyl-, 4-phenylbutyl-, or 5-phenylpentyl group.

A $C_1$-$C_6$ alkyl group: A straight or branched alkyl group with 1-6 C atoms, such as a methyl, ethyl, n-propyl, iso-propyl, n-, iso-, tert-butyl, n-pentyl, 2,2-dimethylpropyl or 3-methylbutyl group.

A cycloalkyl radical: A cyclopropane, cyclobutane, cyclopentane, cyclohexane, cycloheptane, or decahydronaphthalene radical.

A cycloalkylalkyl radical: A cyclopropyl, cyclobutyl, cyclopentyl, cyclohexyl, cycloheptyl-methyl radical; a 1-cyclopropyl, 1-cyclobutyl, 1-cyclopentyl, 1-cyclohexyl, 1-cycloheptyl-ethyl radical; a 2-cyclopropyl, 2-cyclobutyl, 2-cyclopentyl, 2-cyclohexyl, or 2-cycloheptyl-ethyl radical.

A heterocyclic ring: An unsubstituted 2- or 3-thienyl group or a 2- or 3-furyl group or a 3-methyl-, 3-ethyl-, 3-fluoro-, 3-chloro-, 3-bromo-, 3-iodo-2-furyl- or -2-thienyl group; a 4-methyl-, 4-ethyl, 4-fluoro-, 4-chloro-, 4-bromo-, 4-iodo-2-furyl or -2-thienyl group; a 5-methyl-, 5-ethyl-, 5-fluoro-, 5-chloro-, 5-bromo-, 5-iodo-2-furyl- or -2-thienyl group; a 2-methyl, 2-ethyl, 2-fluoro-, 2-chloro-, 2-bromo-, 2-iodo-3-furyl or -3-thienyl group; a 4-methyl-, 4-ethyl-, 4-fluoro-, 4-chloro-, 4-bromo-, 4-iodo-3-furyl- or -3-thienyl group; a 5-methyl-, 5-ethyl-, 5-fluoro-, 5-chloro-, 5-bromo-, 5-iodo-3-furyl- or -3-thienyl group; an unsubstituted 2-, 3- or 4-pyridyl group or a 3-methyl-, 3-ethyl-, 3-fluoro-, 3-chloro-, 3-bromo-, 3-iodo-2-pyridyl group; a 4-methyl-, 4-ethyl-, 4-fluoro-, 4-chloro-, 4-bromo-, 4-iodo-2-pyridyl group; a 5-methyl-, 5-ethyl-, 5-fluoro-, 5-chloro-, 5-bromo-, 5-iodo-2-pyridyl group; a 2-methyl-, 2-ethyl-, 2-fluoro-, 2-chloro-, 2-bromo-, 2-iodo-3-pyridyl group; a 4-methyl-, 4-ethyl-, 4-fluoro-, 4-chloro-, 4-bromo-, 4-iodo-3-pyridyl group; a 5-methyl-, 5-ethyl-, 5-fluoro-, 5-chloro-, 5-bromo-, 5-iodo-3-pyridyl group; a 2-, 4-, 5-, 6-pyrimidinyl group; a 3-, 4-, 5-, 6-pyridazinyl group or a 2- or 3-pyrazinyl group.

R2 means:

An alkyl group: A straight or branched alkyl group with 1-6 C atoms, such as a methyl, ethyl, n-propyl, iso-propyl, n-, iso-, tert-butyl, n-pentyl, 2,2-dimethylpropyl or 3-methylbutyl group. A hydrogen atom is preferred.

An optionally substitutedphenyl ring or naphthyl ring: a phenyl group; an o-, m-, p-methyl, -ethyl, -propyl-, isopropylphenyl group; a 2,3-, 2,4-, 2,5-, 2,6-, 3,4-, 3,5-dimethyl- or -diethylphenyl group; an o-, m-, p-fluoro-, chloro-, bromo-, or iodophenyl group; a 2,3-, 2,4-, 2,5-, 2,6-, 3,4-, 3,5-difluoro-, dichloro-, dibromo- or diiodophenyl group; an o-, m-, p-trihalomethylphenyl group; a 2,3-, 2,4-, 2,5-, 2,6-, 3,4- or 3,5 di-trihalogen-phenyl group; an o-, m-, p-methoxy, -ethoxy, -propoxy, -isopropoxyphenyl group or a naphthyl group. A 2,5-difluorophenyl group is preferred.

R3 and R4 mean:
An alkyl group: A straight or branched alkyl group with 1-6 C atoms, such as a methyl, ethyl, n-propyl, iso-propyl, n-, iso-, tert-butyl, n-pentyl, 2,2-dimethylpropyl- or 3-methylbutyl group. A hydrogen atom is preferred.

R5 means:
An alkyl group: A straight or branched alkyl group with 1-6 C atoms, such as a methyl-, ethyl-, n-propyl-, iso-propyl-, n-, iso-, tert-butyl-, n-pentyl-, 2,2-dimethylpropyl- or 3-methylbutyl group. A hydrogen atom is preferred.

R6 means:
An alkyl group: A straight or branched alkyl group with 1-6 C atoms, such as a methyl-, ethyl-, n-propyl-, iso-propyl-, n-, iso-, tert-butyl-, n-pentyl-, 2,2-dimethylpropyl- or 3-methylbutyl group. A methyl group is preferred.

An aralkyl group with 7-20 C atoms: A benzyl group; a 1-phenyl-ethyl-, -propyl-, -butyl-, -hexyl-, -2-methylethyl-, -2-ethylethyl-, or -2,2-dimethylethyl group; an o-, m-, p-methyl-, ethyl-, propyl-, or iso-propylbenzyl group; a 2',3'-, 2',4'-, 2',5'-, 2',6'-, 3',4'-, 3',5'-dimethyl- or -diethylbenzyl group; a 2'-, 3'-, 4'-fluoro-, chloro-, bromo-, or iodobenzyl group; a 2',3'-, 2',4'-, 2',5'-, 2',6'-, 3',4'-, 3',5'-, difluoro-, dichloro-, dibromo- or diiodobenzyl group or a 2- or 3-naphthylmethyl group; a 2-phenylethyl-, 3-phenylpropyl-, 4-phenylbutyl, or 5-phenylpentyl group.

A heteroaralkyl group with 7-20 C atoms: A 2-, 3- or 4-pyridyl-methyl-, -ethyl- or -propyl group; a 2- or 3-furyl-methyl-, -ethyl-, or -propyl group; a 2- or 3-thienyl-methyl-, -ethyl- or -propyl group; a 2-, 3-, 4-, 5-, 6-, or 7-indolyl-methyl-, -ethyl- or -propyl group. The benzyl group is preferred.

Preferred are compounds of formula (I), in which
—W=X=Y— is the group

If R1 is group —CO—R11, then R11 has, for example, the preferred meaning of methyl, ethyl, i-propyl, phenyl, 2-thienyl and 2-furyl. If R1 has the meaning of —CO—OR12, then R12 can be, for example, preferably methyl, ethyl or i-propyl.

In addition, compounds are preferred in which R2 is an aromatic group, e.g., a benzyl group, for example a 2',6'-difluorobenzyl group, that is substituted on the aromatic ring by one or more halogen atoms, especially fluorine atoms. Also preferred are compounds in which at least one of $R^3$ and $R^4$, especially both, are hydrogen atoms.

A preferred meaning of Z is a direct bond or an oxygen atom, while G preferably means a —C≡C— group. L is preferably an NH group, while Q preferably is a carbonyl group and R51 is a $C_1$-$C_6$ alkyl group. Especially preferred meanings of R61 are hydrogen atoms or $C_1$-$C_3$ alkyl groups, especially methyl groups, and an especially preferred meaning of R62 is an aralkyl radical, e.g., a benzyl group.

The production of compounds (1) is preferably carried out
(a) By reaction of a compound of general formula (2)

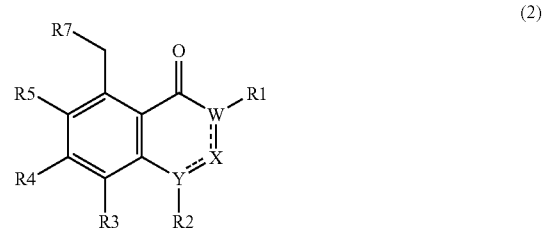

whereby R7 means a leaving group, e.g., a halogen atom or an alkyl, perfluoroalkyl or arylsulfonyl group, and all other radicals have the meaning that is indicated in compound (1), with a compound of general formula (3)

R8-N(R61)R62     (3)

whereby R8 means a hydrogen atom or a metal atom, such as, e.g., a lithium, sodium, potassium, cesium, calcium or barium atom, and R61 and R62 have the meanings that are indicated in compound (1), (b) By reaction of a compound of general formula (4)

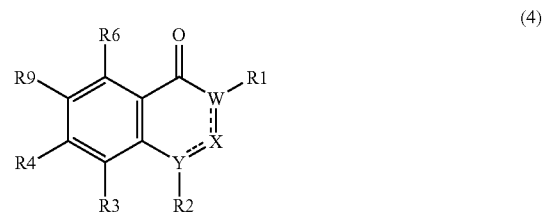

in which R9 is the group —$OSO_2C_nF_{2n+1}$, a halogen atom, especially a bromine or iodine atom, or another leaving group, and all other radicals have the meaning that is indicated in compound (1), with a compound of general formula (5)

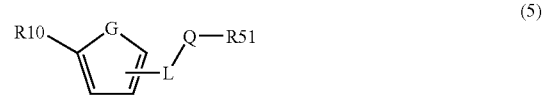

whereby R10 is a group that contains a metal, such as a group that contains a trialkyltin group, a halomagnesium group or a group that contains a non-metal, such as boron, silicon, etc.; a dialkoxyboron group or a dihydroxyboron group; a hydroxy or mercapto group that is optionally converted into a metal salt, such as, e.g., a lithium, sodium, potassium, cesium, calcium, barium, silver or copper salt; the group —C≡C—R31 or an E- or Z-configured group —CR52=CR53R31 or —CR31=CR52R53, in which R31 is a group that contains a metal or a non-metal, such as boron, silicon, etc., such as a trialkyltin group, a halomagnesium group, a dialkoxyboron group or a dihydroxyboron group, and all other radicals have the meaning that is indicated in compound (1), with or without the involvement of a catalyst, such as, e.g., copper, nickel, palladium, platinum or organic derivatives of the above-mentioned metals;

(c) If Y is a nitrogen atom in compound (1), by reaction of a compound of general formula (6)

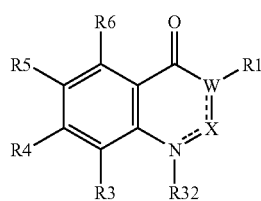

(6)

whereby R32 means a hydrogen atom or a metal atom, such as, e.g., a lithium, sodium, potassium, cesium, calcium, barium, silver or copper atom, and all other radicals have the meaning that is indicated in compound (1), with a compound of general formula (7)

R33-R2  (7)

whereby R33 means a leaving group, e.g., a halogen atom or an alkyl, perfluoroalkyl or arylsulfonyl group, and R2 has the meaning that is indicated in compound (1)

or (d) If W in compound (1) is a nitrogen atom, by reaction of a compound of general formula (8)

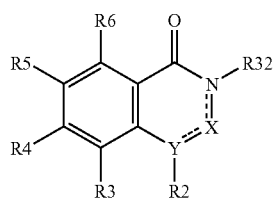

(8)

whereby R32 means a hydrogen atom or a metal atom, such as, e.g., a lithium, potassium, cesium, calcium, barium, silver or copper atom, and another radicals have the meaning that is indicated in compound (1), with a compound of general formula (9)

R33-R1  (9)

whereby R33 means a leaving group, e.g., a halogen atom or an alkyl, perfluoroalkyl or arylsulfonyl group, and R1 has the meaning that is indicated in compound (1).

Compounds (1) according to the invention can be used as antagonists of the gonadotropin-releasing hormone, for example for male birth control, for hormone therapy, for treatment of female subfertility and infertility, for female contraception and to combat tumors.

In male birth control, the compounds according to the invention bring about a reduction in spermatogenesis. A combined administration with androgens, e.g., testosterone or testosterone derivatives, such as, for example, testosterone esters, preferably takes place. The administration of testosterone derivatives can be carried out, for example, by injection, e.g., by intramuscular depot injection.

Compounds (1), optionally in combination with other hormones, e.g., estrogens and/or progestins, can also be used in hormone therapy, for example for treating endometriosis, uterus leiomyomas and uterine fibroids. Especially preferred are combinations of the GnRH antagonists according to the invention and tissue-selective partial estrogen agonists such as Raloxifene®. Moreover, compounds (1) according to the invention can be used for increasing female fertility, for example by inducing ovulation, and treating sterility.

In contrast, compounds (1) are also suitable for contraception in females. Thus, the GnRH antagonist can be administered on days 1 to 15 of the cycle together with estrogen, preferably with very low estrogen dosages. On days 16 to 21 of the intake cycle, progestagen is added to the estrogen-GnRH-antagonist combination. The GnRH antagonist can be administered continuously over the entire cycle time. In this way, a reduction in the hormone dosages and thus a reduction in the side effects of unphysiological hormone levels can be achieved. In addition, advantageous effects in women who suffer from polycystic ovarian syndrome and androgen-dependent diseases, such as acne, seborrhea and hirsutism, can be achieved. An improved cycle monitoring relative to previous administration methods can also be expected. Further indications are benign prostate hyperplasia, gonad protection in chemotherapy, controlled ovarian stimulation/artificial reproduction techniques, and infantile development disorders, e.g., Pubertas praecox and polycystic ovaries.

Finally, the GnRH agonists according to the invention can also be used for the treatment of hormone-dependent tumor diseases, such as premenopausal breast cancer, prostate cancer, ovarian cancer and endometrial cancer, by the endogenous sex steroid hormones being suppressed.

Compounds (1) according to the invention are suitable as GnRH antagonists for administration to humans, but also for the purposes of veterinary medicine, e.g., in the case of domestic and working animals but also in the case of wild animals.

The administration can be carried out in the known way, for example, orally, topically, rectally, intravaginally, nasally or by injections. Oral administration is preferred. Compounds (1) are brought into a form that can be administered and are optionally mixed with pharmaceutically acceptable vehicles or diluents. The oral administration can be carried out, for example, in solid form as tablets, capsules, coated tablets or powders, but also in the form of a drinkable solution. The non-oral administration can be carried out by, for example, intravenous, subcutaneous or intramuscular injection or by ointments, creams or suppositories. An administration as a timed-release form can optionally also be carried out. The dosage can vary depending on the type of indication, the severity of the disease, the age, sex, body weight and sensitivity of the subject to be treated. Dosages of 0.01 to 30 mg, especially preferably 0.1 to 3 mg, and most preferably 0.1 to 1 mg per kg of body weight and per day are preferably administered. The administration can be carried out in an individual dose or several separate dosages.

Below, a number of especially preferred compounds (1) are listed:

Especially Preferred Compounds

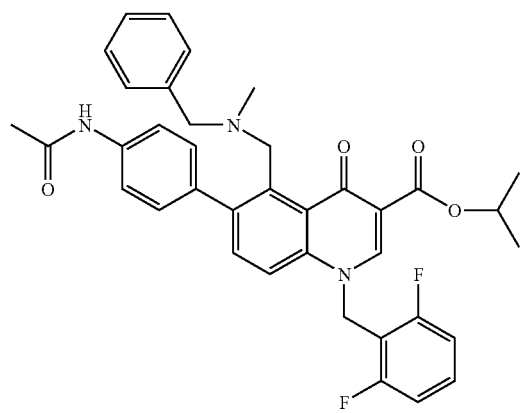

6-(4-Acetamidophenyl)-5-(N-benzyl-N-methylaminomethyl)-1-(2',6'-difluorobenzyl)-1,4-dihydro-4-oxo-quinoline-3-carboxylic acid-2-propyl ester

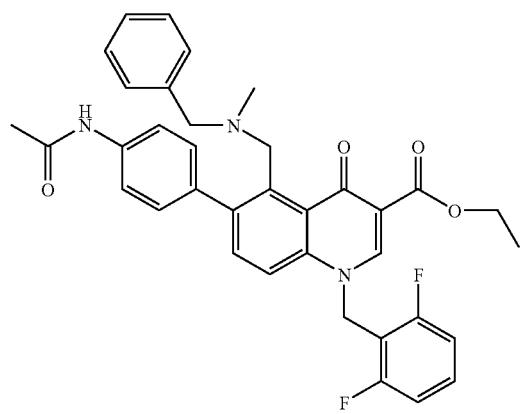

6-(4-Acetamidophenyl)-5-(N-benzyl-N-methylaminomethyl)-1-(2',6'-difluorobenzyl)-1,4-dihydro-4-oxo-quinoline-3-carboxylic acid ethyl ester

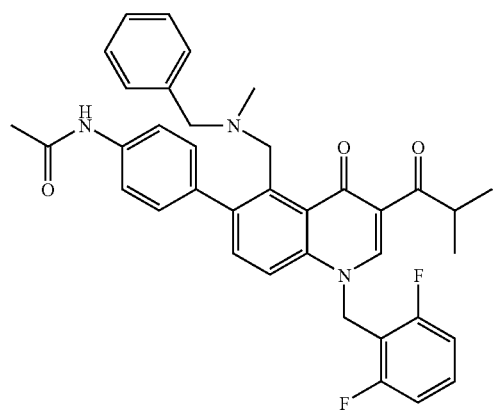

6-(4-Acetamidophenyly-3-isobutyryl-5-(N-benzyl-N-methylaminomethyl)-1-(2',6'-difluorobenzyl)-1,4-dihydro-4-oxo-quinoline -continued

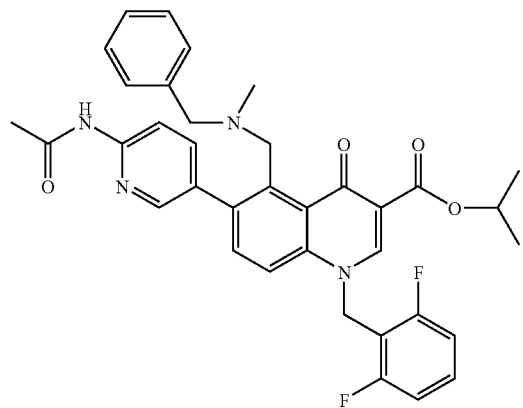

6-(2-Acetamido-5-pyridyl)-5-(N-benzyl-N-methylaminomethyl)-1-(2',6'-difluoro-benzyl)-1,4-dihydro-4-oxo-quinoline-3-carboxylic acid-isopropyl ester

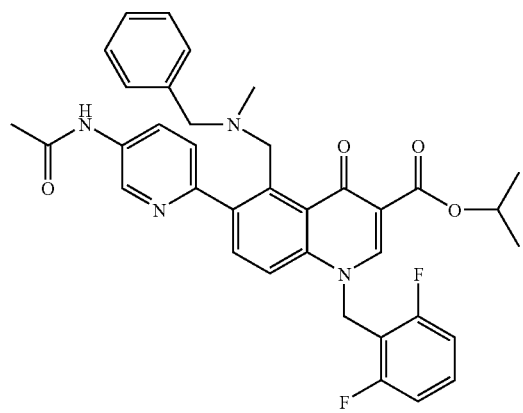

6-(3-Acetamido-6-pyridyl)-5-(N-benzyl-N-methylaminomethyl)-1-(2',6'-difluoro-benzyl)-1,4-dihydro-4-oxo-quinoline-3-carboxylic acid 2-propyl ester

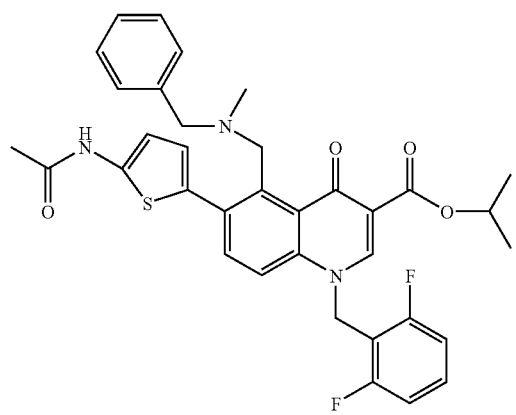

6-(5-Acetamido-2-thienyl)-5-(N-benzyl-N-methylaminomethyl)-1-(2',6'-difluoro-benzyl)-1,4-dihydro-4-oxo-quinoline-3-carboxylic acid-2-propyl ester

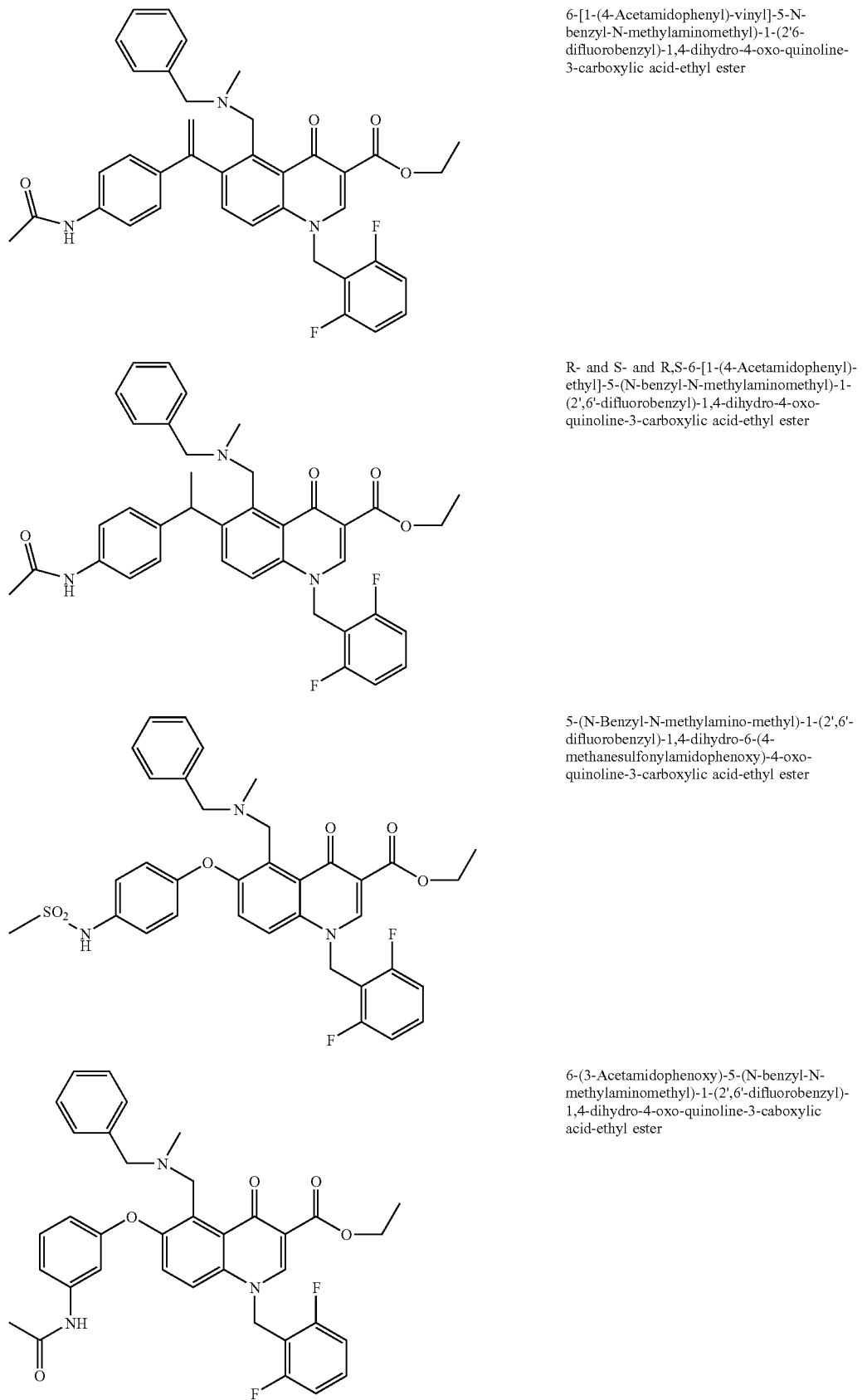

6-[1-(4-Acetamidophenyl)-vinyl]-5-N-benzyl-N-methylaminomethyl)-1-(2'6-difluorobenzyl)-1,4-dihydro-4-oxo-quinoline-3-carboxylic acid-ethyl ester R- and S- and R,S-6-[1-(4-Acetamidophenyl)-ethyl]-5-(N-benzyl-N-methylaminomethyl)-1-(2',6'-difluorobenzyl)-1,4-dihydro-4-oxo-quinoline-3-carboxylic acid-ethyl ester 5-(N-Benzyl-N-methylamino-methyl)-1-(2',6'-difluorobenzyl)-1,4-dihydro-6-(4-methanesulfonylamidophenoxy)-4-oxo-quinoline-3-carboxylic acid-ethyl ester 6-(3-Acetamidophenoxy)-5-(N-benzyl-N-methylaminomethyl)-1-(2',6'-difluorobenzyl)-1,4-dihydro-4-oxo-quinoline-3-caboxylic acid-ethyl ester

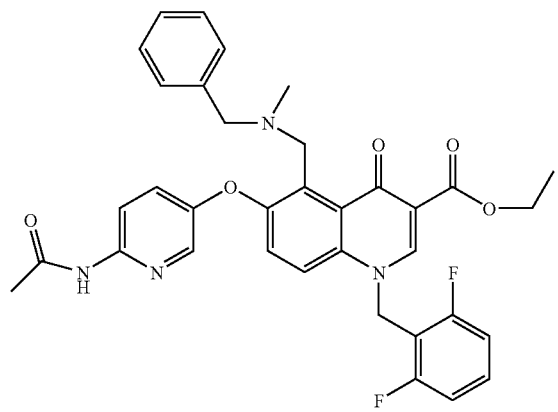

6-(2-Acetamido-5-pyridyloxy)-5-(N-benzyl-N-methylaminomethyl)-1-(2',6'-difluorobenzyl)-1,4-dihydro-4-oxo-quinoline-3-carboxylic acid-ethyl ester

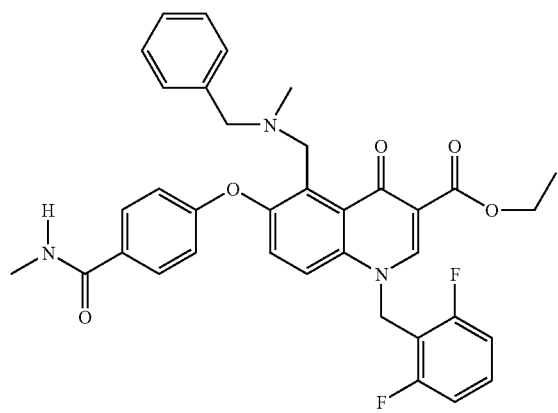

6-(2-Methylaminocarbonyl-5-pyridyloxy)-5-(N-benzyl-N-methylaminomethyl)-1-(2',6'-difluorobenzyl)-1,4-dihydro-4-oxo-quinoline-3-carboxylic acid-ethyl ester

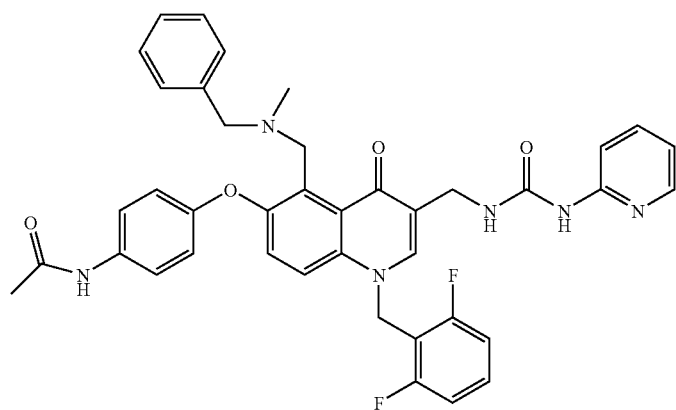

1-[6-(4-Acetamidophenoxy)-5-(N-benzyl-N-methylaminomethyl)-1-(2',6'-difluorobenzyl)-1,4-dihydro-4-oxo-quinolin-3-yl)-methyl]-3-pyridin-2-yl-urea

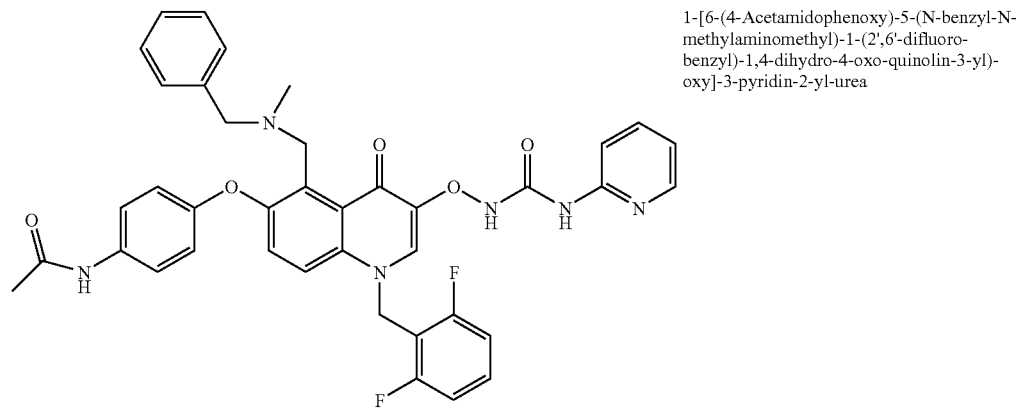

1-[6-(4-Acetamidophenoxy)-5-(N-benzyl-N-methylaminomethyl)-1-(2',6'-difluoro-benzyl)-1,4-dihydro-4-oxo-quinolin-3-yl)-oxy]-3-pyridin-2-yl-urea

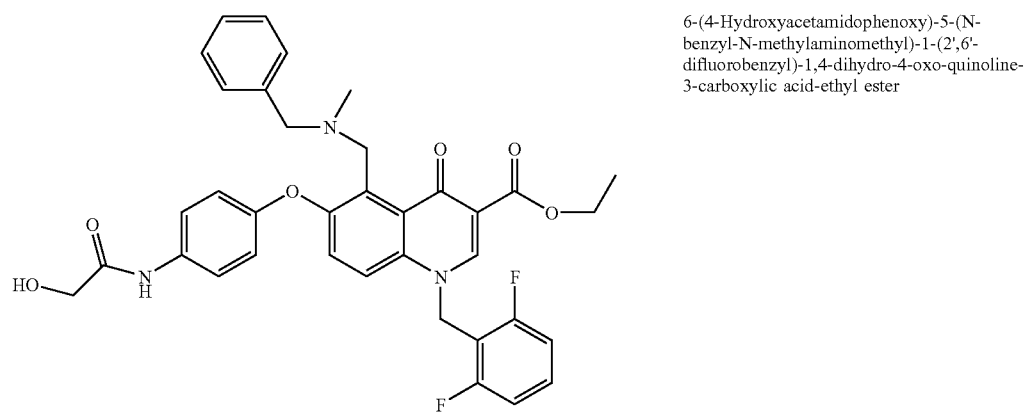

6-(4-Hydroxyacetamidophenoxy)-5-(N-benzyl-N-methylaminomethyl)-1-(2',6'-difluorobenzyl)-1,4-dihydro-4-oxo-quinoline-3-carboxylic acid-ethyl ester

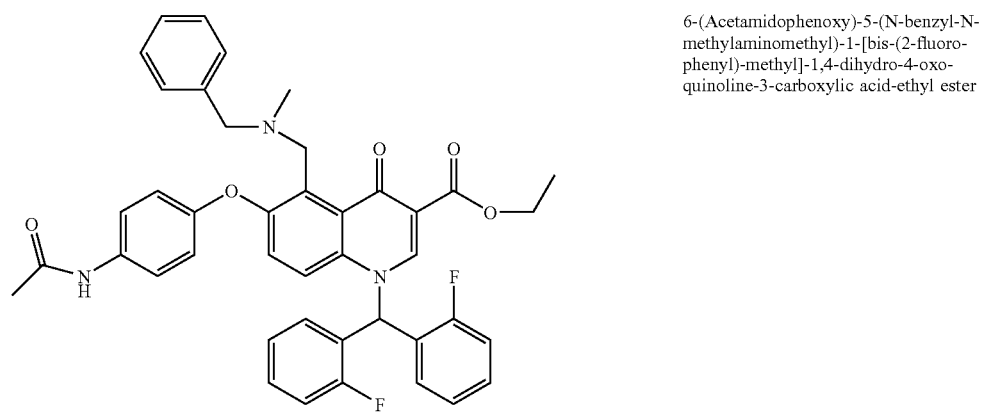

6-(Acetamidophenoxy)-5-(N-benzyl-N-methylaminomethyl)-1-[bis-(2-fluoro-phenyl)-methyl]-1,4-dihydro-4-oxo-quinoline-3-carboxylic acid-ethyl ester

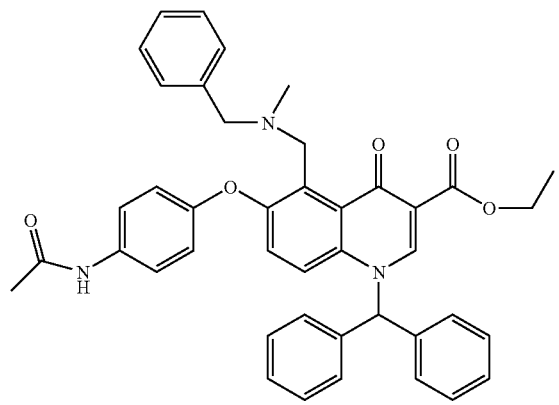

6-(Acetamidophenoxy)-5-(N-benzyl-N-methylaminomethyl)-1-diphenylmethyl-1,4-dihydro-4-oxo-quinoline-3-carboxylic acid-ethyl ester In addition, the invention is to be explained by the following examples.

EMBODIMENTS

Example 1

6-(4-Acetamidophenoxy)-5-(N-benzyl-N-methylaminomethyl)-1-(2',6'-difluorobenzyl)-1,4-dihydro-4-oxo-quinoline-3-carboxylic acid-ethyl ester

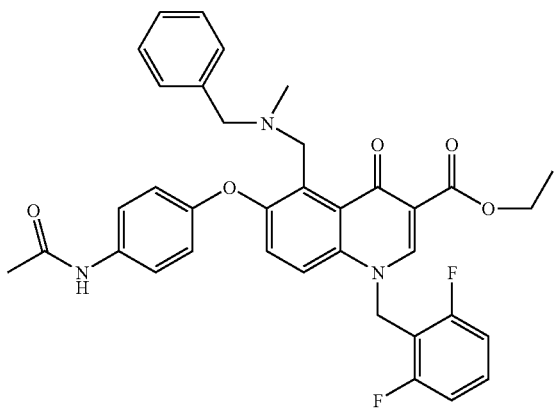

78 mg of 6-(4-acetamidophenoxy)-5-(chloromethyl)-1-(2',6'-difluorobenzyl)-1,4-dihydro-4-oxo-quinoline-3-carboxylic acid-ethyl ester, dissolved in 3 ml of dimethylformamide, was mixed with 84 μl of N-methylbenzylamine and 84 μl of N,N-diisopropyl-ethylamine at 0° C. and stirred at room temperature for 20 hours. After 20 ml of aqueous sodium bicarbonate solution was added, the precipitate was suctioned off, washed with water and then with n-hexane, and dried at room temperature in a vacuum. 70 mg of the title compound is obtained.

NMR:=1.3 (t; 3H; $CH_3$); 1.9 (s; 3H; $NCH_3$); 2.05 (s; 3H; $CH_3$); 3.55 (s; 2H; $NCH_2$); 4.27 (q; 2H; $OCH_2$); 4.91 (s; 2H; $NCH_2$); 5.68 (s; 2H; $NCH_2$); 6.85 (d; 2H; ArCH); 7.1-7.22 (m; 7H; ArCH); 7.26 (d; 1H; ArCH); 7.42-7.6 (m; 4H; ArCH); 8.72 (s; 1H; NCH); 9.9 (s; 1H; NH)

MS: FAB: $M^{\oplus}+1=526$ [M=525]

The starting material, 6-(4-acetamidophenoxy)-5-(chloromethyl)-1-(2',6'-difluorobenzyl)-1,4-dihydro-4-oxo-quinoline-3-carboxylic acid ethyl ester, was obtained in the following way:

a. 1,4-Dihydro-6-fluoro-5-nitro-4-oxo-quinoline-3-carboxylic acid ethyl ester

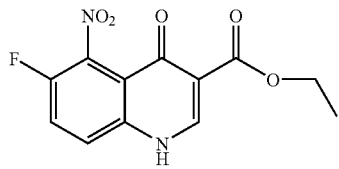

50 g of 4-fluoro-3-nitroaniline and 69 g of ethoxymethylene malonic acid-diethyl ester were heated for 3 hours to 120° C. The mixture was added to n-hexane, stirred for 2 hours, and the crystalline material was suctioned off and dried in a vacuum at room temperature. 93 g of N-(4-fluoro-3-nitrophenyl)-aminomethylene malonic acid diethyl ester is obtained. The latter is added in 3 portions of 31 g to respectively 150 ml of a mixture that consists of 26.5% diphenyl and 73.5% diphenyl ether (DOWTHERM A$^{\oplus}$) that is preheated to 260° C., and it is stirred for 30 minutes at this temperature. After cooling, it is diluted with 500 ml of n-hexane, and the precipitate is suctioned off. A total of 64 g of a mixture of 1,4-dihydro-6-fluoro-5-nitro-4-oxo-quinoline-3-carboxylic acid ethyl ester and 1,4-dihydro-6-fluoro-7-nitro-4-oxo-quinoline-3-carboxylic acid-ethyl ester is obtained.

NMR:=1.31 (t; 3H; $CH_3$); 4.25 (q; 2H; $OCH_2$); 7.88 (s; 1H; ArCH; isomer A); 7.92 (s; 1H; ArCH; isomer A); 8.1 (d; 1H; ArCH; isomer B); 8.45 (d; 1H; ArCH; isomer B); 8.59+8.69 (2s; 1H each; NCH; A+B)

MS: EI: $M^{\oplus}=280$ [M=280]

b. 1-(2',6'-Difluorobenzyl)-1,4-dihydro-6-fluoro-5-nitro-4-oxo-quinoline-3-carboxylic acid ethyl ester

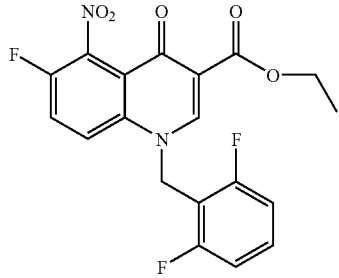

22 g of the above-described mixture is stirred in 500 ml of dimethylformamide with 16 g of potassium carbonate and 23.7 g of 2,6-difluorobenzyl bromide for 5 hours at room temperature. The reaction mixture is added to 1 l of aqueous ammonium chloride solution and extracted three times with ethyl acetate. After drying with sodium sulfate and concentration by evaporation in a vacuum, 500 ml of n-hexane is added, and it is stirred for 15 minutes. After the hexane phase is decanted, the residue is recrystallized from ethyl acetate. 10.4 g of the title compound is obtained.

NMR:=1.3 (t; 3H; CH$_3$); 4.25 (q; 2H; OCH$_2$); 5.84 (s; 2H; NCH$_2$); 7.15-7.25 (m; 2H; ArCH); 7.45-7.55 (m; 1H; ArCH); 7.92 (dd; 1H; ArCH); 8.04-8.14 (m; 1H; ArCH); 8.96 (s; 1H; NCH);

MS: EI: M$^\oplus$=406 [M=406]

c. 6-(4-Acetamidophenoxy)-1-(2',6'-difluorobenzyl)-1,4-dihydro-5-nitro-4-oxo-quinoline-3-carboxylic acid ethyl ester

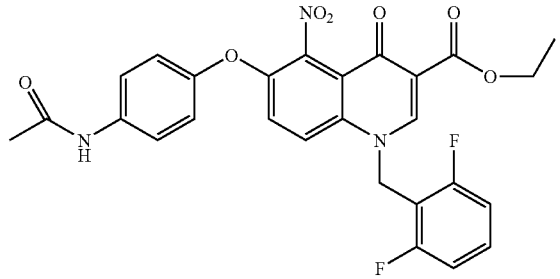

3.74 g of 4-acetamidophenol in 40 ml of dimethylformamide is mixed with 733 mg of sodium hydride (80% in mineral oil) and stirred for 15 minutes at room temperature. Then, this solution is added to 5 g of the above-described compound, dissolved in 40 ml of dimethylformamide. After 5 hours at room temperature, the mixture is added to ice water, and the precipitate is suctioned off. After chromatography on silica gel (eluant dichloromethane/2-propanol 95:5), 5.17 g of the title compound is obtained.

NMR:=1.3 (t; 3H; CH$_3$); 2.03 (s; 3H; CH$_3$); 4.27 (q; 2H; OCH$_2$); 5.79 (s; 2H; NCH$_2$); 7.01 (d; 2H; ArCH); 7.13-7.23 (m; 2H; ArCH); 7.43-7.56 (m; 2H; ArCH); 7.61 (d; 2H; ArCH); 7.8 (d; 1H; ArCH); 8.93 (s; 1H; NCH); 9.97 (1H; S; NH)

MS: EI: M$^\oplus$=537 [M=537]

d. 6-(4-Acetamidophenoxy)-5-amino-1-(2',6'-difluorobenzyl)-1,4-dihydro-4-oxo-quinoline-3-carboxylic acid-ethyl ester

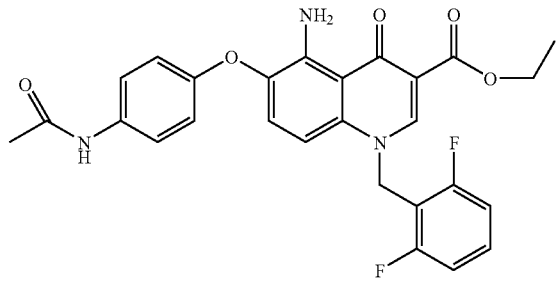

5.1 g of the above-mentioned compound is hydrogenated in 650 ml of methanol with 510 mg of palladium/carbon (10%). After the catalyst is suctioned off and after concentration by evaporation, 4.55 g of the title compound is obtained.

NMR:=1.29 (t; 3H; CH$_3$); 2.02 (s; 3H; CH$_3$); 3.25 (s; 2H; NH$_2$); 4.25 (q; 2H; OCH$_2$); 5.55 (s; 2H; NCH$_2$); 6.55 (d; 1H; ArCH); 6.86 (d; 2H; ArCH); 7.07 (d; 1H; ArCH); 7.1-7.22 (m; 2H; ArCH); 7.4-7.55 (m; 3H; ArCH); 8.71 (s; 1H; NCH); 9.8 (s; 1H; NH);

MS: EI: M$^\oplus$=507 [M=507]

e. 6-(4-Acetamidophenoxy)-1-(2',6'-difluorobenzyl)-1,4-dihydro-5-iodo-4-oxo-quinoline-3-carboxylic acid-ethyl ester

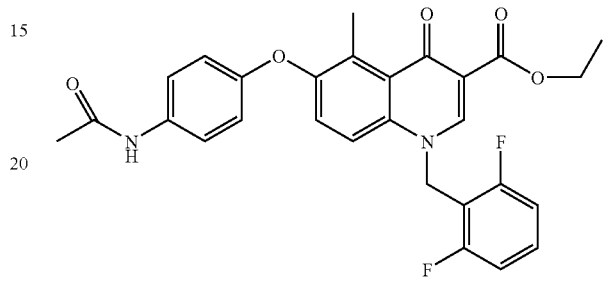

2 g of the above-mentioned compound is dissolved in a mixture of 24 ml of concentrated sulfuric acid and 12 ml of water, and it is mixed at 0° C. with 325 mg of sodium nitrite in 4 ml of water. After 15 minutes, a pH of 3 is set with sodium bicarbonate solution, and 100 mg of urea is added. Then, 723 mg of potassium iodide in 0.5 ml of water is added, and it is stirred for one hour at room temperature. After extraction with dichloromethane/methanol (95:5, v/v), the organic phase is washed with aqueous sodium thiosulfate solution, dried and concentrated by evaporation. After chromatography on silica gel (eluant dichloromethane with 0-15% isopropanol), 697 mg of the title compound is obtained.

NMR:=1.3 (t; 3H; CH$_3$); 2.02 (s; 3H; CH$_3$); 4.25 (q; 2H; OCH$_2$); 5.71 (s; 2H; NCH$_2$); 6.83 (d; 2H; ArCH); 7.1-7.2 (2H; m; ArCH); 7.3 (d; 1H; ArCH); 7.41-7.63 (m; 4H; ArCH); 8.83 (s; 1H; N-CH); 9.95 (s; 1H; NH)

MS: es: M$^\oplus$+1=493 [M=492]

f. 6-(4-Acetamidophenoxy)-1-(2',6'-difluorobenzyl)-1,4-dihydro-4-oxo-5-styryl-quinoline-3-carboxylic acid-ethyl ester

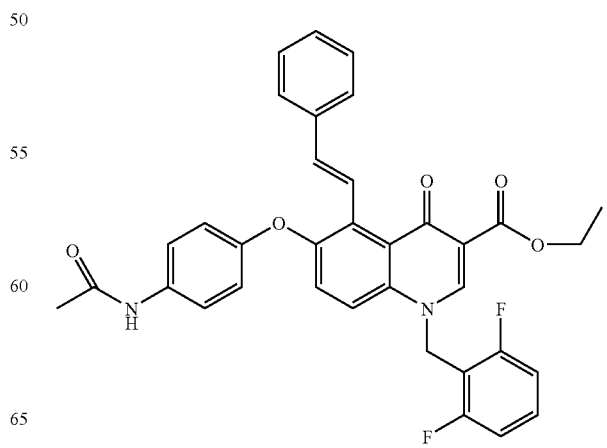

550 mg of the above-mentioned iodine compound, 198 mg of styrylboronic acid, 55 mg of tetrakis-triphenylphosphine-palladium(O), 1.1 ml of 2 molar sodium carbonate solution, 2.2 ml of ethanol and 22 ml of toluene are stirred for 6 hours at 80° C. Then, water is added, extracted with dichloromethane, and the organic phase is washed with common salt solution, dried and concentrated by evaporation. The residue is purified by chromatography on silica gel (eluant dichoromethane with 0-10% isopropanol). 902 mg of the title compound is obtained.

NMR: =1.28 (t; 3H; CH$_3$); 2.0 (s; 3H; CH$_3$); 4.24 (q; 2H; OCH$_2$); 5.7 (s; 2H; N—CH$_2$); 6.75-6.85 (m; 3H; ArCH; CH=CH); 7.08-7.28 (m; 3H; ArCH); 7.3-7.68 (m; 9H; ArCH); 7.86 (d; 1H; CH=CH); 8.75 (S; 1H; NCH); 9.72 (1H; S; NH)

MS: es: M$^\oplus$+1=595 [M=594]

g. 6-(4-Acetamidophenoxy)-1-(2',6'-difluorobenzyl)-1,4-dihydro-5-formyl-4-oxo-quinoline-3-carboxylic acid-ethyl ester

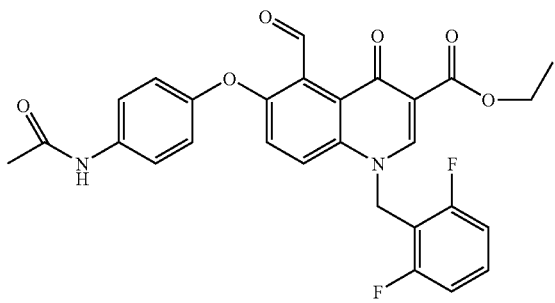

450 mg of the above-mentioned styryl compound is dissolved in 25 ml of tetrahydrofuran and 7 ml of water, and it is mixed with 0.11 ml of a 2.5% solution of osmium tetroxide in tert-butanol. After 15 minutes of stirring at room temperature, 482 mg of sodium periodate is added; after 20 and 22 hours, 100 mg of sodium periodate is added; and after 24 hours, another 100 mg of sodium periodate is added. After 26 hours, it is diluted with water and extracted with ethyl acetate. After the organic phase is dried with sodium sulfate, it is concentrated by evaporation. 352 mg of the title compound is obtained as a foam.

NMR:=1.29 (t; 3H; CH$_3$); 2.01 (s; 3H; CH$_3$); 4.27 (q; 2H; OCH$_2$); 5.71 (s; NCH$_2$); 6.91 (d; 2H; ArCH); 7.12-7.22 (m; 2H; ArCH); 7.4 (d; 1H; ArCH); 7.43-7.64 (m; 3H; ArCH); 7.72 (d; 1H; ArCH); 9.0 (d; 1H; NCH); 9.97 (s; 1H; NH); 10.44 (s; 1H; CHO)

MS: FAB: M$^\oplus$+1=521 [M=520]

h. 6-(4-Acetamidophenoxy)-1-(2',6'-difluorobenzyl)-1,4-dihydro-5-hydroxymethyl-4-oxo-quinoline-3-carboxylic acid-ethyl ester

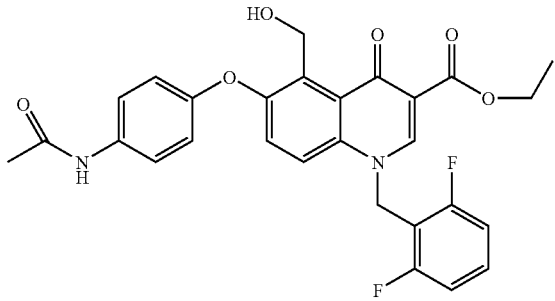

300 mg of the above-mentioned aldehyde is dissolved in 13.8 ml of acetic acid and mixed at 10-minute intervals with 3 portions of 10 mg of sodium borohydride each. After dilution with water, it is extracted with ethyl acetate, and the organic phase is washed neutral with sodium bicarbonate solution. After drying with sodium sulfate, it is concentrated by evaporation. By chromatography on silica gel (eluant dichloromethane with 0-10% isopropanol), 129 mg of the title compound is obtained as a foam.

MNR:=1.31 (t; 3H; CH$_3$); 2.02 (s; 3H; CH$_3$); 4.27 (q; 2H; OCH$_2$); 4.86 (d; 2H; OCH$_2$); 5.12 (t; 1H; OH); 5.8 (s; 2H; NCH$_2$); 6.85 (d; 2H; ArCH); 7.12-7.22 (m, 2H; ArCH); 7.38 (d; 1H; ArCH); 7.42-7.59 (m; 3H; ArCH); 7.63 (d; 1H; ArCH); 8.94 (s; 1H; NCH); 9.5 (s; 1H, NH)

MS: FAB: M$^\oplus$+1=523 [M=522]

i. 6-(4-Acetamidophenoxy)-5-chloromethyl-1-(2',6'-difluorobenzyl)-1,4-dihydro-4-oxo-quinoline-3-carboxylic acid-ethyl ester

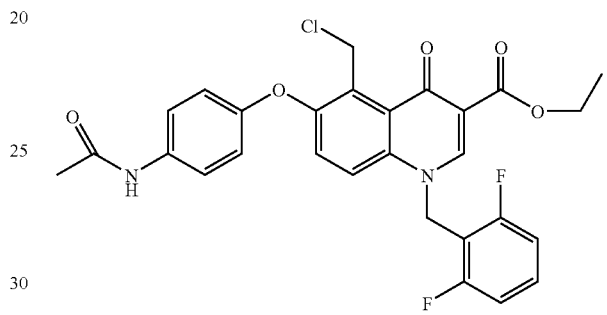

80 mg of the above-mentioned alcohol is dissolved in 2 ml of dichloromethane and mixed with 0.1 ml of thionyl chloride. After 20 minutes at room temperature, water is added, it is extracted with dichloromethane, and the organic phase is washed with common salt solution. After drying with sodium sulfate, it is concentrated by evaporation. 80 mg of the title compound is obtained as a foam.

NMR:=1.33 (t; 3H; CH$_3$); 2.07 (s; 3H; CH$_3$); 4.3 (q; 2H; OCH$_2$); 5.66 (s; 2H; CH$_2$Cl); 5.75 (s; 2H; NCH$_2$); 6.98 (d; 2H; ArCH); 7.13-7.25 (m; 2H; ArCH); 7.3 (d; 1H; ArCH); 7.53 (t; 1H; ArCH); 7.61 (d; 2H; ArCH); 7.68 (d; 1H; ArCH); 8.82 (s; 1H; NCH); 9.98 (s; 1H; NH)

MS: es: M$^\oplus$+1=541/543 [M=540/542]

Example 2

6-(4-Acetamidophenoxy)-5-(N-benzyl-N-methylaminomethyl)-1-(2',6'-difluoro-benzyl)-1,4-dihydro-4-oxo-quinoline-3-carboxylic acid-2-propyl ester

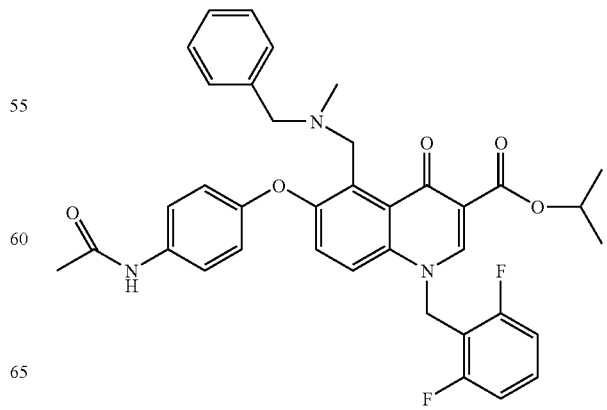

This compound is produced from 6-(4-acetamidophenoxy)-5-(N-benzyl-N-methylaminomethyl)-1-(2',6'-difluorobenzyl)-1,4-dihydro-4-oxo-quinoline-3-carboxylic acid ethyl ester by heating with titanium-tetraisopropylate in isopropanol.

Example 3

5-(N-Benzyl-N-methylaminomethyl)-1-(2',6'-difluorobenzyl)-1,4-dihydro-6-(4-isobutyramidophenoxy)-4-oxo-quinoline-3-carboxylic acid-ethyl ester

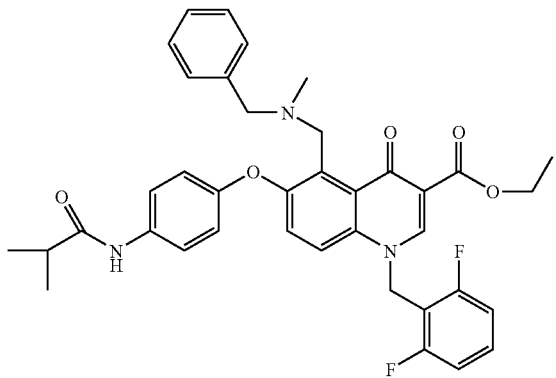

This compound is produced analogously to Example 1 from 5-(chloromethyl)-1-(2',6'-difluorobenzyl)-1,4-dihydro-6-(4-isobutyramidophenoxy)-4-oxo-quinoline-3-carboxylic acid-ethyl ester and N-methylbenzylamine as a foam.

a. 5-(Chloromethyl)-1-(2',6'-difluorobenzyl)-1,4-dihydro-6-(4-isobutyramidophenoxy)-4-oxo-quinoline-3-carboxylic acid-ethyl ester

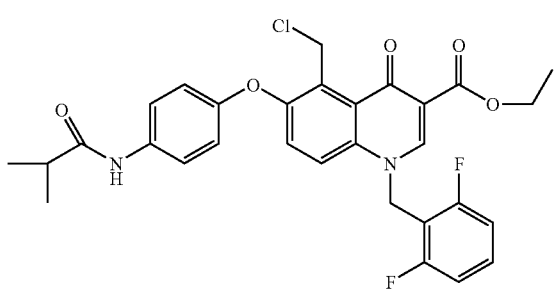

This compound is obtained when, in Example 1/c, 4-isobutyramidophenol is used instead of 4-acetamidophenol and the rest of the reaction is carried out as described in Example 1/d. to Example 1/i.

Example 4

3-Acetyl-6-(4-acetamidophenyl)-1-benzyl-5-(N-benzyl-N-methylaminomethyl)-phthalazin-4-one

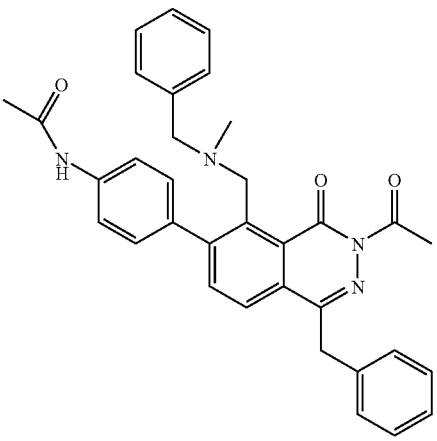

The title compound is obtained by 6-(4-acetamidophenyl)-1-benzyl-5-(N-benzyl-N-methylaminomethyl)-phthalazin-4-one being reacted in the presence of a base such as sodium carbonate or sodium hydroxide with acetyl chloride or acetic anhydride.

6-(4-Acetamidophenyl)-1-benzyl-5-(N-benzyl-N-methylaminomethyl)-phthalazin-4-one is obtained in the following way:

a. 6-(4-Acetamidophenyl)-1-benzyl-5-iodo-phthalazin-4-one

1-Benzyl-5,6-diiodo-phthalazin-4-one (Indian J. Chem. 16B, 1978, 301-304) is reacted analogously to Example 1/f. with 1 equivalent of 4-acetamidophenyl-boronic acid. The title compound is obtained in pure form by chromatography on silica gel.

b. 6-(4-Acetamidophenyl)-1-benzyl-5-chloromethyl-phthalazin-4-one

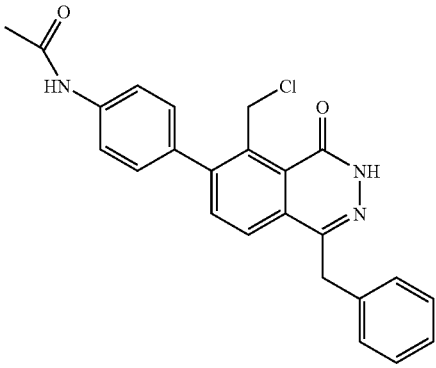

6-(4-Acetamidophenyl)-1-benzyl-5-iodo-phthalazin-4-one is further reacted to form the title compound analogously to Example 1/f.-i.

Example 5

6-(4-Acetamidophenoxy)-5-(N-benzyl-N-methylamino-methyl)-1,4-dihydro-4-oxo-1-(2'-trifluoromethylbenzyl)-quinoline-3-carboxylic acid-ethyl ester

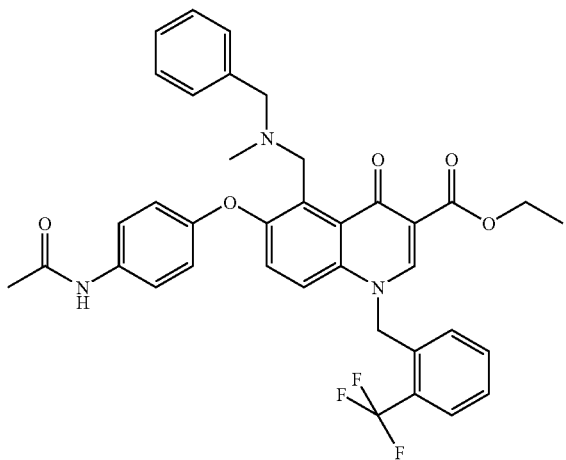

130 mg (0.226 mmol) of 6-(4-acetamidophenoxy)-5-(chloromethyl)-1,4-dihydro-4-oxo-1-(2'-trifluoromethyl-benzyl)-quinoline-3-carboxylic acid-ethyl ester, dissolved in 5 ml of DMF, is mixed at −5° C. with 125 µl of N,N-diisopropyl-ethylamine and 126 µl (0.97 mmol) of N-benzyl-methylamine. After heating to room temperature, it is allowed to stir for 20 more hours, and then the reaction mixture is added to 50 ml of saturated sodium bicarbonate solution. The solid is suctioned off, washed with water and dried in a vacuum. The additional purification is carried out by chromatography on silica gel with an eluant that consists of 90 parts of dichloromethane, 10 parts of ethanol and 1 part of concentrated ammonia ($R_f$:0.38).2.

45 mg of the title compound is obtained as a foam.

MS/molar peak, $M^+$=658

The starting material 6-(4-acetamidophenoxy)-5-(chloromethyl)-1,4-dihydro-4-oxo-1-(2'-trifluoromethylbenzyl)-quinoline-3-carboxylic acid-ethyl ester is produced analogously to the method that is described in Examples 1a to 1i with use of 2'-trifluoromethyl-benzyl bromide instead of 2,6-difluoromethylbenzyl bromide.

Example 6

6-(4-Methylaminocarbonyl-phenoxy)-5-(N-benzyl-N-methylaminomethyl)-1-(2',6'-difluorobenzyl)-1,4-dihydro-4-oxo-quinoline-3-carboxylic acid-ethyl ester 35 mg (0.061 mmol) of 6-(4-methylaminocarbonyl-phenoxy)-5-(chloromethyl)-1-(2',6'-difluorobenzyl)-1,4-dihydro-4-oxo-quinoline-3-carboxylic acid-ethyl ester, dissolved in 1.3 µl of DMF, is mixed at 0° C. with 35 µl of N,N-diisopropyl-ethylamine and 35 µl (0.25 mmol) of N-methylbenzylamine. After heating to room temperature, it is allowed to stir for 20 more hours, and then the reaction mixture is added to 10 ml of saturated sodium bicarbonate solution. The accumulated solid is suctioned off, washed with water and hexane and dried on phosphorus pentoxide in a vacuum.

27 mg of the title compound is obtained as a foam.

MS (esi): $M^+$+1=626 [M=625]

The starting material 6-(4-methylaminocarbonyl-phenoxy)-5-(chloromethyl)-1-(2',6'-difluorobenzyl)-1,4-dihydro-4-oxo-quinoline-3-carboxylic acid-ethyl ester is produced analogously to the method that is described in Examples 1a to 1i with use of 4-hydroxy-N-methylbenzoic acid amide instead of 4-acetamidophenol.

Example 7

6-(4-Acetamidophenoxy)-5-(N-benzyl-N-methylamino-methyl)-1-(1-naphthyl-methyl)-1,4-dihydro-4-oxo-quinoline-3-carboxylic acid-ethyl ester 45 mg (0.081 mmol) of 6-(4-acetamidophenoxy)-5-(chloromethyl)-1-(1-naphthylmethyl)-1,4-dihydro-4-oxo-quinoline-3-carboxylic acid-ethyl ester, dissolved in 1.7 ml of DMF, is mixed at 0° C. with 46 µl of N,N-diisopropyl-ethylamine and 46 µl (0.33 mmol) of N-methylbenzylamine. After heating to room temperature, it is allowed to stir for 20 more hours, and then the reaction mixture is added to 15 ml of saturated sodium bicarbonate solution. The accumulated solid is suctioned off, washed with water and hexane and dried on phosphorus pentoxide in a vacuum.

32 mg of the title compound is obtained as a foam.

MS (esi): $M^+$+1=639 [M=638]

The starting material 6-(4-acetamidophenoxy)-5-(chloromethyl)-1-(1-naphthyl-methyl)-1,4-dihydro-4-oxo-quinoline-3-carboxylic acid-ethyl ester is produced analogously to the method that is described in Examples 1a to 1i with use of 1-chloromethylnaphthalene instead of 2,6-difluoromethylbenzyl bromide.

Example 8

Detection of the Antagonistic Action a) Materials

Buserelin was ordered from Welding (Frankfurt/Main, Germany). The compound was labeled with $^{125}$I by use of the chloramine T-method and Na$^{125}$I (4000 Ci/mmol; Amersham-Buchler, Brunswick, Germany). The labeled substance was purified by reverse phase HPLC on a Spherisorb ODS II column (250×4 mm, particle size 3 µm) by elution with 50% acetonitrile/0.15% trifluoroacetic acid at a flow rate of 0.5 ml/min. The specific activity was 2000 Ci/mmol.

All other chemicals were ordered from commercial sources at the highest available purity.

b) Cell Culture

Alpha T3-1 cells (Bilezikjian et al., Mol. Endocrinol 5 (1991), 347-355) were cultivated in DMEM medium (Gibco-BRL, Eggenstein-Leopoldshafen, Germany) with penicillin (100 I.U./ml), streptomycin (0.1 mg/ml) and glutamine (0.01 mol/l) and 10% fetal calf serum (FCS; PAA Laboratories, Coelbe, Germany) on plastic tissue culture plates (Nunc, 245×245×20 mm). CHO-3 cells (Schmid et al., J. Biol. Chem. 275 (2000), 9193-9200) were cultivated under identical conditions, apart from the fact that Ham's F12 medium (Gibco-BRL) was used.

Ten confluent cell culture plates were flushed twice with 50 ml of phosphate-buffered salt solution (PBS). The cells were harvested by scraping them off with a rubber scraper in 5 ml of PBS and sedimented by centrifuging in a laboratory centrifuge (Heraeus) at 800 rpm for 10 minutes. The cell pellet was resuspended in 5 ml of 0.25 mol/l of saccharose/ 0.01 mol/l of triethanolamine, pH 7.4. The cells were lysed by three cycles of freezing in dry ice/ethanol bath and thawing at room temperature. The lysate was centrifuged at 900 rpm for 10 minutes, and the sediment was discarded. The supernatant was centrifuged at 18,000 rpm in a Sorvall SS34 rotor for 30 minutes. The pellet (cell membranes) was suspended by Potters in 5 ml of assay buffer (0.25 ml/l of saccharose, 0.01 mol/l of triethanolamine, pH 7.5, 1 mg/ml of ovalbumin) and stored in 200 µl of aliquots at −20° C. The determination of protein was carried out according to the Bradford method (Anal. Biochem. 72 (1976), 248-254).

c) Receptor Assay

Binding studies for competition curves were performed as triplicates. A test sample contained 60 µl of cell membrane suspension (10 µg of protein for αT3-1 cells or 40 µg of protein for CHO3 cells), 20 µl of $^{125}$I-labeled buserelin (100,000 Ipm per sample for competition curves and between 1,500 and 200,000 Ipm for saturation experiments) and 20 µl of test buffer or test compound solution. The test compounds were dissolved in distilled water or 50% ethanol. Ser. dilutions (5×10$^{-6}$ mol/l to 5×10$^{-12}$ mol/l) were produced in test buffer. The unspecific binding was determined in the presence of excess unlabeled buserelin (10$^{-6}$ mol/l). The test samples were incubated for 30 minutes at room temperature. Bonded and free ligands were separated by filtration (Whatman GF/C-filter, 2.5 cm diameter) with use of an Amicon 10×collecting device and washed twice with 5 ml of 0.02 mol/l Tris/HCl, pH 7.4. The filters were moistened with 0.3% polyethylenimine (Serva; Heidelberg, Germany) for 30 minutes to reduce the unspecific binding. The radioactivity that was held up by the filter was determined in a 5-channel gamma-counter (Wallac-LKB 1470 Wizard).

What is claimed is:

1. A compound of general formula (I):

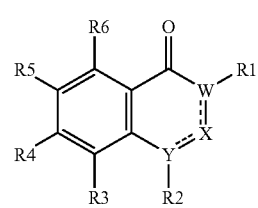

wherein

R1 (a) is an acyl group —CO—R11, wherein R11 is methyl, or
  b) is a carboxylic acid ester group —CO—OR12, wherein R12 is a straight or branched alkyl chain with 1-10 atoms, R2 is a group —CH(R21)R22, wherein R21 is a hydrogen atom, a $C_1$-$C_{10}$-alkyl group or an optionally substituted phenyl ring and R22 is an optionally substituted phenyl ring or naphthyl ring, or a group —CH$_2$CH(R23)R24, wherein R23 and R24 are an optionally substituted phenyl ring, R3 and R4, in each case independently, are a hydrogen atom or an alkyl group with 1-10 C atoms, and R3 also can be a halogen atom, R5 is a group that is linked via radical Z,

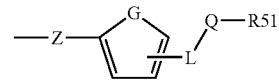

in which G is —C=C—, Z is a direct bond, the group CH—R52 or —CHR52—CH—R53-, wherein R52 and R53, independently of one another, have the meaning of a hydrogen atom, an alkyl group, a —C≡C-triple bond, L is an NH group, Q is a carbonyl group, and R51 is a straight or branched alkyl group that is optionally substituted by halogen atoms, hydroxyl or alkoxy groups, R6 is the group CH$_2$—N(R61)R62, wherein R61, in each case independently, is a hydrogen atom or an alkyl group, and R62 is an optionally substituted aralkyl group with 7-20 C atoms, and —W=X=Y— is the group

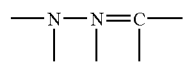

in any orientation;
or a salt thereof with a pharmaceutically acceptable acid or base.

2. A compound according to claim 1, wherein R1 is —CO—R11.

3. A compound according to claim 1, wherein R1 is —CO—OR12.

4. A compound according to claim 3, wherein R12 is methyl, ethyl, or i-propyl.

5. A compound according to claim 1, wherein R2 is 2',5'-difluorobenzyl.

6. A compound according to claim 1, wherein R3 and R4 are hydrogen atoms.

7. A compound according to claim 1, wherein Z is a direct bond.

8. A compound according to claim 1, wherein R61 is hydrogen or methyl and/or R62 is benzyl.

9. A process for preparing a compound of formula (1) according to claim 1, comprising:

(a) reacting a compound of general formula (2)

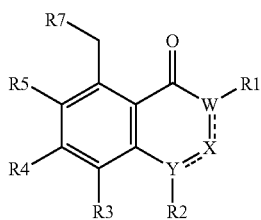

(2)

wherein R7 means a leaving group,
with a compound of general formula (3)

R8-N(R61)R62        (3)

wherein R8 means a hydrogen atom or a metal atom, (b) reacting a compound of general formula (4)

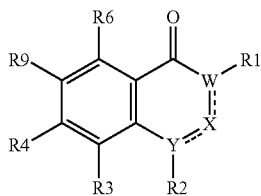

(4)

wherein R9 is the group —OSO$_2$C$_n$F$_{2n+1}$ where n is 1 or 2, a halogen atom, or another leaving group,
with a compound of general formula (5)

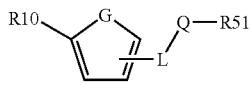

(5)

wherein R10 is a group that contains a metal or a non-metal, a hydroxy or mercapto group that is optionally converted into a metal salt; the group —C≡C—R31 or an E- or Z-configured group —CR52=CR53R31 or —CR31=CR52R53, wherein R31 is a group that contains a metal or a non-metal, with or without the involvement of a catalyst;

(c) wherein if Y is a nitrogen atom in compound (1), reacting a compound of formula (6)

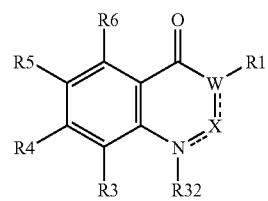

(6)

wherein R32 means a hydrogen atom or a metal atom, with a compound of general formula (7)

R33-R2        (7)

wherein R33 means a leaving group, or (d) if W in compound (1) is a nitrogen atom, reacting a compound of general formula (8)

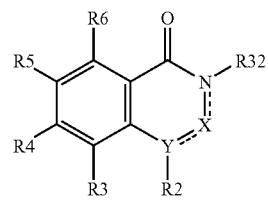

(8)

wherein R32 means a hydrogen atom or a metal atom, with a compound of general formula (9)

R33-R1        (9)

wherein R33 means a leaving group.

10. A pharmaceutical composition comprising a compound according to claim 1 and a pharmaceutically acceptable carrier.

11. A compound according to claim 1, wherein R52 and R53 are, independently, a straight or branched alkyl group with 1-6 atoms.

12. A compound according to claim 1, which is a stereoisomer of a compound of formula I.

13. 3-Acetyl-6-(4-acetamidophenyl)-1-benzyl-5-(N-benzyl-N-methylaminomethyl)-phthalazin-4-one;
or a salt thereof with a pharmaceutically acceptable acid or base.

* * * * *

UNITED STATES PATENT AND TRADEMARK OFFICE
CERTIFICATE OF CORRECTION

PATENT NO. : 7,378,522 B2  Page 1 of 1
APPLICATION NO. : 10/896961
DATED : May 27, 2008
INVENTOR(S) : Peter Strehlke It is certified that error appears in the above-identified patent and that said Letters Patent is hereby corrected as shown below:

Column 30, line 2 claim 1 reads "A compound of general formula" should read --A compound of formula--
Column 30, line 20 claim 1 reads "1-10 atoms" should read --1-10 C atoms--
Column 31, line 27 claim 9 reads "reacting a compound of general formula" should read --reacting a compound of formula--
Column 31, line 42 claim 9 reads "with a compound of general formula" should read --with a compound of formula--
Column 32, line 23 claim 9 reads "compound of general formula" should read --compound of formula--
Column 32, line 36 claim 9 reads "compound of general formula" should read --compound of formula--

Signed and Sealed this

Thirtieth Day of December, 2008

JON W. DUDAS
*Director of the United States Patent and Trademark Office*